(12) United States Patent
Havlina

(10) Patent No.: US 6,329,177 B1
(45) Date of Patent: Dec. 11, 2001

(54) ENZYMATIC METHODS OF PREPARING POLYMERS FROM NUCLEOTIDE AND/OR NON-NUCLEOTIDE MONOMERS

(75) Inventor: Roxana Maria Havlina, Bereholz-Rehbrücke (DE)

(73) Assignee: Larova Biochemie GmbH, Teltow (DE)

(*) Notice: Subject to any disclaimer, the term of this patent is extended or adjusted under 35 U.S.C. 154(b) by 0 days.

(21) Appl. No.: 09/338,124

(22) Filed: Jun. 22, 1999

(30) Foreign Application Priority Data

Jun. 22, 1998 (DE) .............................. 198 27 728

(51) Int. Cl.[7] .............................. C12Q 1/68; C12P 19/34; C07H 19/00; C07H 21/00
(52) U.S. Cl. ............................ 435/91.1; 435/6; 536/22.1; 536/25.3; 536/25.32
(58) Field of Search ............................ 435/6, 91.1, 91.2; 536/22.1, 25.3, 25.32

(56) References Cited

U.S. PATENT DOCUMENTS

| 3,300,478 | 1/1967 | Wechter | 260/211.5 |
| 5,750,341 | * 5/1998 | Macevicz | 435/6 |

FOREIGN PATENT DOCUMENTS

| 5-292967 | 2/1994 | (JP) . |
| 94/14972 | 7/1994 | (WO) . |
| 96/41809 | 12/1996 | (WO) . |

OTHER PUBLICATIONS

McConnell, T.S. et al., "Guanosine Binding to the Tetrahymena Ribozyme: Thermodynamic Coupling with Oligonucleotide Binding", *Proc. Natl. Acad. Sci. U.S.A.*, vol. 90, No. 18 (1993), pp. 8362–8366.

Shevchenko, N.M. et al., "Synthesis of Modified Triuridylates by the H–Phosphonate Method", *Bioorg. Khim.*, vol. 14, No. 7, (1988), pp. 976–978 (English Abstract Only).

Holy, A. et al., "Effect of 5'–Substitution on the Template Activity of Oligonucleotides for the Binding of Valine and Alanine tRNA to Ribosomes", *Biochim. Biophys. Acta.*, vol. 217, No. 2, (1970), pp. 332–345.

Kleinwachter V. et al., "Luminescence Properties of Dinucleoside Phosphates, Some Oligonucleotides, and Polynucleotides", *Collect. Czech. Chem. Commun.*, vol. 37, No. 10 (1972), pp. 3433–3446.

Vratskikh, L.V. et al., "Solid–Phase Synthesis of Oligoribonucleotides Using T4 RNA Ligase and T4 Polynucleotide Kinase", *Biochimie*, vol. 77, No. 4 (1995) pp. 227–232.

* cited by examiner

*Primary Examiner*—Jezia Riley
(74) *Attorney, Agent, or Firm*—Fish & Richardson PC

(57) ABSTRACT

There is described the preparation of polymers from nucleotide and/or non-nucleotide monomers, in particular the preparation of natural and/or base-modified and/or sugar-modified and/or phosphate group-modified oligodeoxyribonucleotides and/or oligoribonucleotides and/or non-nucleotide polymers in an enzymatic manner in 3'→5' direction using a RNA ligase.

22 Claims, 5 Drawing Sheets

Method for the preparation of oligonucleotides in 5' → 3' direction according to Hyman

3. Method for the preparation of polymers from deoxyribonucleotide and/or non-nucleotide monomers 4. Method for the preparation of polymers from ribonucleotide and/or non-nucleotide monomers

FIG.4

1st and 2nd method for the preparation of polymers

FIG.5

3rd and 4th method for the preparation of polymers

ENZYMATIC METHODS OF PREPARING POLYMERS FROM NUCLEOTIDE AND/OR NON-NUCLEOTIDE MONOMERS

CROSS REFERENCE TO RELATED APPLICATIONS

This application claims benefit from German application serial number 198 27 728.8, filed Jun. 22, 1998, which is incorporated herein by reference in its entirety.

FIELD OF THE INVENTION

The invention is directed to the preparation of natural and/or modified polymers having a defined sequence consisting of nucleotide and/or non-nucleotide monomers in an enzymatic manner.

TECHNICAL BACKGROUND

Synthetic oligonucleotides and polynucleotides having a defined sequence are of use in diagnostics and as therapeutics, for example as antisense oligonucleotides, ribozymes or aptamers.

Oligonucleotides may be prepared using chemical or enzymatic methods. The enzymatic method as an alternative of the conventional chemical process is gaining more and more importance. Known enzymatic techniques proceed in 5'→3' direction.

For the preparation of oligonucleotides in an enzymatic manner, the following chain elongating enzymes may be used:

a terminal transferase,
a polynucleotide phosphorylase,
a RNA ligase, or
a DNA polymerase (EP 0 491 739 B1).

Terminal transferase, i.e. terminal deoxynucleotidyl transferase (EC 2.7.7.31), catalyses the addition of deoxynucleotide triphosphates to the 3'-OH terminal of single or double stranded DNA in a template-independent reaction.

Polynucleotide phosphorylase (EC 2.7.7.8) catalyses a number of reactions, among them the 5'→3'-polymerization which involves ribonucleoside 5'-diphosphates.

RNA ligase (EC 6.5.1.3) catalyses a covalent linkage between a 5'-phosphate donor and a 3'-hydroxy acceptor in the presence of ATP.

It is obvious from the reaction mechanism of RNA ligase that an ATP dependent and an ATP independent step can be distinguished in the course the reaction steps. First, the enzyme binds a molecule of ATP at the ATP binding site, and in a first reaction step AMP is covalently linked to the enzyme with simultaneous release of $PP_i$. The donor is bound by its enzyme binding site via the 5'-terminal nucleoside and the two neighbouring phosphate groups. Then, in the second reaction step, donor activation may occur by transfer of the enzyme-bound AMP to the 5'-terminal phosphate group of the donor while the phosphoanhydride bond is formed. Donor activation takes place in an ATP-dependent step. In the third step of the reaction the internucleosidic bond between acceptor and donor is formed while AMP is released. Ligation of the activated donor A-5'-pp5'-N to the acceptor is ATP independent. Both reaction steps may also proceed in a manner independent of each other.

The enzymatic synthesis of oligoribonucleotides in 5'→3'-direction is known. In the variant of the synthesis according to Hyman /1/ the acceptor and an adenylated nucleoside 3',5'-bisphosphate with a phosphate protecting group in 3'-position are presented to RNA ligase as the activated donor. This reaction is illustrated by the scheme shown in FIG. 1.

Figure 1:
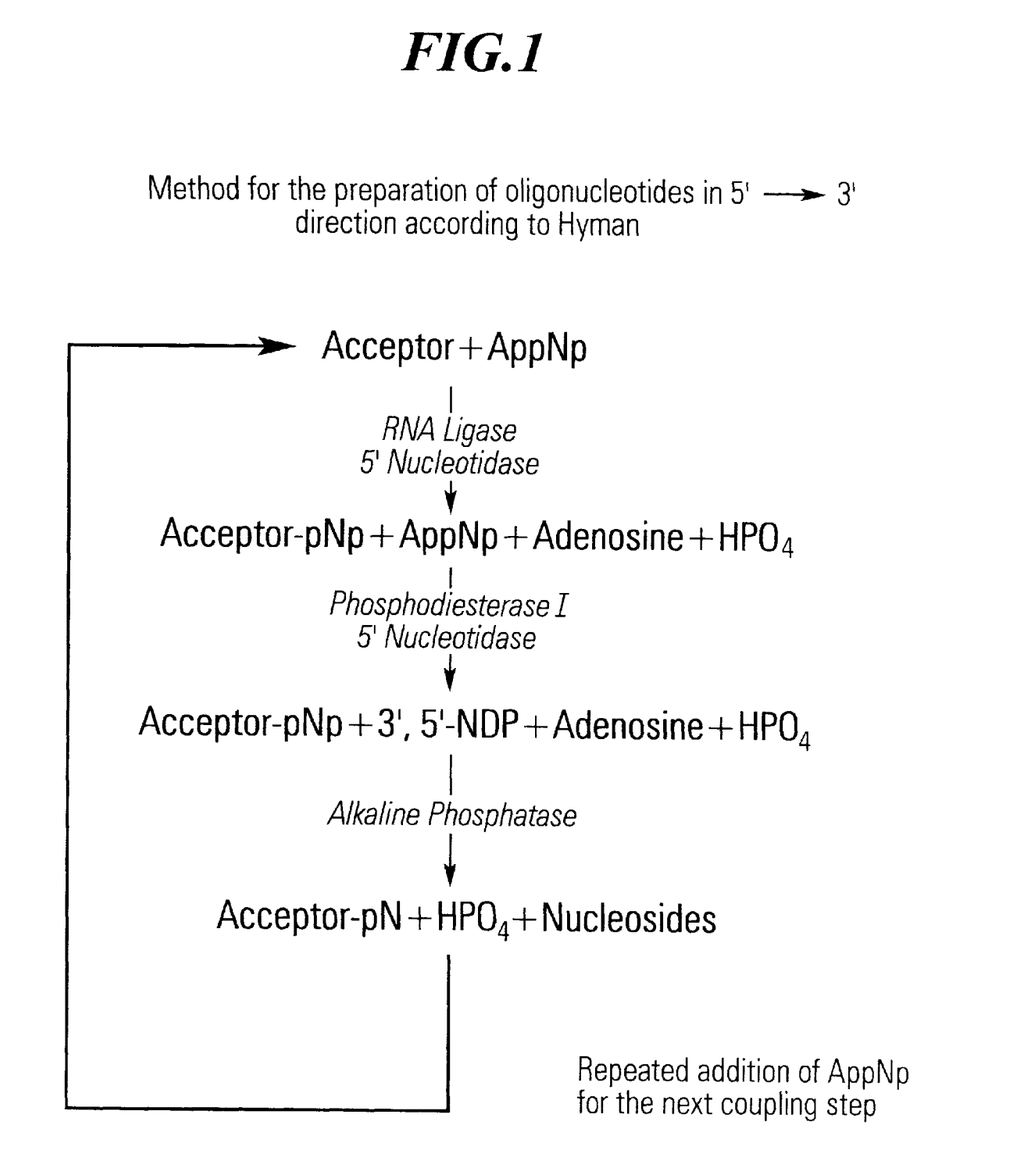
FIG. 1 is a flow chart that illustrate a method for the preparation of oligonucleotides in the 5' to 3' direction.

The abbreviations in FIG. 1 have the following meanings:
AppNp an activated donor, a nucleotide having a phosphate protecting group in 3'-position,
pNp a nucleotide having a phosphate protecting group in 3'-position,
pN a nucleotide without protecting group in 3'-position.

The method of Hyman is well suited for the synthesis of natural and modified oligoribonucleotides.

For the synthesis of oligodeoxyribonucleotides, Hyman proposes to synthesize a complementary oligoribonucleotide according to his method and
to convert the oligoribonucleotide into a oligodeoxyribonucleotide using reverse transcriptase /1/2/.

Other methods describe the amplification of a template using DNA polymerase I /3/4/.

These known methods bear several disadvantages.

The first disadvantage is that no oligonucleotides with alternating sequences, such as with natural phosphodiester or thiophosphate bonds or with natural ribose residues or 2'-alkyl substituted ribose residues, may be prepared but only a uniform monomer type may be polymerized.

The second disadvantage is that not the extraordinary broad substrate specificity of RNA ligase for the donor can be used to synthesize a modified product, insofar as the same modification is desired in all monomers, but instead the very limited substrate specificity of reverse transcriptase must be employed.

At the moment, RNA ligase may only be used in the synthesis of natural and modified oligoribonucleotides. The reason for this is the very narrow specificity of RNA ligase for an oligoribonucleotide being the acceptor.

If the newly synthesized growing product is the acceptor, one or two deoxyribonucleotides may be coupled, then the method is no longer practical since RNA ligase is unable to incorporate oligodeoxyribonucleotides as acceptors in the polymerization reaction in 5'→3' direction.

Known studies concerning the enzymatic synthesis of oligodeoxyribonucleotides in 5'→3' direction are limited to complex methods which are impracticable on a technical scale /5/6/.

SUMMARY OF THE INVENTION

The present invention is based on the object of providing novel enzymatic methods for general use using a RNA ligase for the preparation of different polymers from nucleotide and/or non-nucleotide monomers, in particular for the preparation of natural and/or base modified and/or sugar-modified and/or phosphate group-modified oligodeoxyribonucleotides and/or oligoribonucleotides and/or non-nucleotide polymers in 3'→5' direction having a defined monomer sequence. The polymers which may be prepared according to the invention also comprise oligonucleotides and polynucleotides in their most general form. It is another object to provide carrier molecules to carry out the methods.

The solution of these objects will become obvious from the following specification and the claims.

Thus, the invention pertains to novel methods for the preparation of polymers from nucleotide and/or non-nucleotide monomers in 3'→5' direction wherein novel synthetic carriers are used at the same time being carrier molecules of the natural and/or modified monomers to be newly coupled wherein RNA ligase as well as auxiliary enzymes are used, such as an RNase, an uracil DNA glycosylase, an apurinic endonuclease and a polynucleotide kinase.

DETAILED DESCRIPTION

Figure 2:
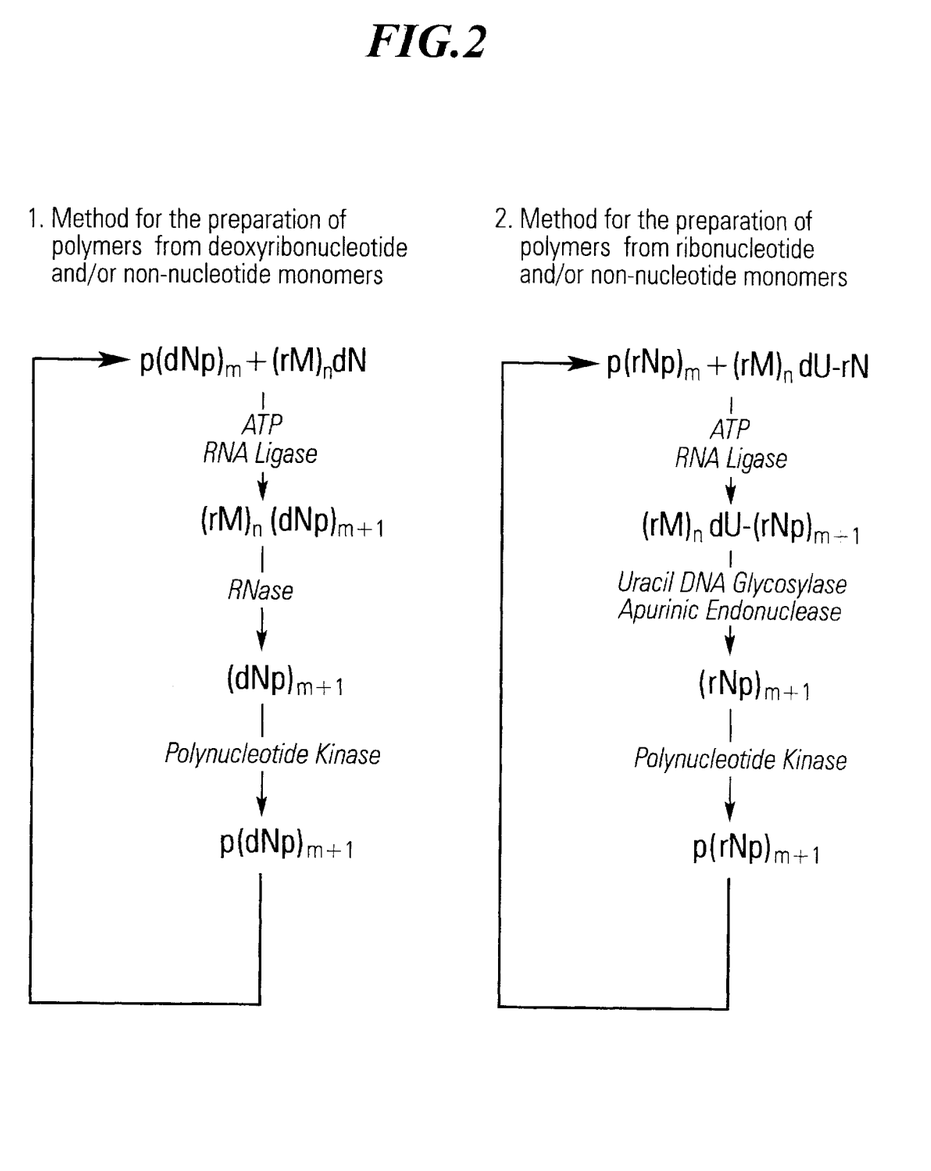
FIG. 2 is a pair of flow charts that illustrate first and second methods of the invention for preparing polymers from deoxyribonucleotide and/or non-nucleotide monomers and from ribonucleotide and/or non-nucleotide monomers.

According to one embodiment, the present invention comprises the cyclic enzymatic methods which are schematically illustrated in FIG. 2 for the preparation of polymers.

The abbreviations in FIG. 2 have the following meanings:

$p(dNp)_m$ primer (in this case the donor) in the method of preparation 1, $p(rNp)_m$ primer (in this case the donor) in the method of preparation 2, $(rM)_n dN$ novel synthetic carrier: the acceptor in the method of preparation 1, $(rM)_n dU\text{-}rN$ novel synthetic carrier: the acceptor in the method of preparation 2, rM a purine and/or pyrimidine ribonucleoside, dU a deoxyuridine, dN a natural and/or base- and/or sugar-modified deoxyribonucleoside and/or a non-nucleosidic ligation-competent group of compounds, rN a natural and/or base- and/or sugar-modified ribonucleoside and/or a non-nucleosidic ligation-competent group of compounds, p a phosphate and/or phosphorothioate and/or phosphonate, such as preferably methyl phosphonate and/or H-phosphonate, and/or phosphorarmidate and/or formylacetal and/or phosphorodithioate and/or boranephosphate and/or phosphotriester group, m an integer of 1 or more, n is zero or an integer of 1 or more.

Starting with the primer (in this case the donor) of the general formula $p(dNp)_m$ or $p(rNp)_m$ having the general structural formula I (I)

$p(dNp)_m$ and $p(rNp)_m$ and the novel synthetic carrier of the invention (in this case the acceptor) of the general formula $(rM)_n dN$ having the general structural formula II (II)

$(rM)_n dN$ or the novel carrier $(rM)_n dU\text{-}rN$ having the general structural formula III (III)

$(rM)_n dU\text{-}rN$ wherein the abbreviations used in the formulas have the following meanings:

m an integer of 1 or more, n is zero or an integer of 1 or more

B a natural and/or modified purine and/or pyrimidine base,

U an uracil, $R^1$ and $R^2$ H, OH O-alkyl, F, J, Br, Cl, amino, aminoalkyl, O-alkoxyalkyl, alkyl X O, S, NH, $-NR^3$ ($R^3 = C_{1\text{-}20}$-alkyl group)

p a phosphate and/or phosphorothioate and/or phosphonate, such as preferably methyl phosphonate and/or H-phosphonate, and/or phosphoramidate and/or formylacetal and/or phosphorodithioate and/or boranephosphate and/or phosphotriester group, wherein may be replaced by a non-nucleosidic ligation competent group of compounds,
first the primer is activated in the ligation step using an RNA ligase, in an amount enabling ligation, and afterwards ligated to the carrier used according to the present invention. Preferably, the carrier used according to the invention of the general formula $(rM)_n dN$ or $(rM)_n dU$-rN is employed in an excess over the primer having the general formula $p(dNp)_m$ or $p(rNp)_m$.

Activation and ligation may occur together or separately.

The nucleoside monomer dN or rN of the carrier used according to the invention having the general formula $(rM)_n dN$ or $(rM)_n dU$-rN which is coupled to the 5'-position of the primer of the general formula $p(dNp)_m$ or $p(rNp)_m$ and is a component of the finally defined sequence lacks a protecting group in its 3'-position.

The carrier used according to the present invention having the general formula $(rM)_n dN$ or $(rM)_n dU$-rN has $(rM)_n$ or $(rM)_n dU$ as the protecting group at its 5'-position, said protecting group being cleaved off in the deprotection step.

The group p mentioned in the 3'-position of the primer of the general formula $p(dNp)_m$ or $p(rNp)_m$ should not be construed as limiting. Preferably, this group can be ommited.

The carrier used according to the present invention having the general formula $(rM)_n dN$ or $(rM)_n dU$-rN has the highest affinity for RNA ligases in the presence of oligoribonucleotide monomers. For this reason, ligation yields of about 100% are achieved. The structure of the carrier used according to the invention is critical for successful 3'→5' ligation in all of the methods of the invention.

The primer and the carrier used according to the present invention may be present in the form of metal salts, preferably alkali metal salts.

Furthermore, the efficiency of the coupling reaction is dependent on several parameters:

1. RNA ligases have a broad pH spectrum in the range of about pH 7.0 to pH 10.0. Preferably, the ligation is carried out at a pH of approx. 8.3. The reaction is effected in a buffered aqueous medium, preferably with HEPES-NaOH or HEPPS-NaOH. Use of HEPPS-NaOH at about 25 mM to 100 mM achieves even higher yields in comparison to HEPES-NaOH.
2. The ligation is carried out in a temperature range of about 4° C. to 40° C., preferably at about 37° C.
3. The ligation reaction will proceed only in the presence of divalent metal ions, preferably with about 10 mM to 20 mM of $Mn^{2+}$ and more preferably in the presence of dithiothreitol (DTT) at about 3 mM to 20 mM.
4. It is preferred to increase the efficiency of the ligation by adding a ligation efficiency increasing amount of dimethylsulfoxide (DMSO), preferably 15% (v/v), or by addition of PEG and hexammine cobalt chloride, preferably 25% (w/v) polyethylene glycol (PEG 6000) and 1 mM of hexammine cobalt chloride.

In the deprotection step in the presence of an RNase, digestion or alkaline cleavage of the $(rM)_n$ protecting group occurs if the carrier having the general formula $(rM)_n dN$ has been used. If the value of n is zero then it is not necessary to cleave off the $(rM)_n$ protecting group since the resulting polymer already has the correct defined sequence. If the carrier having the general formula $(rM)_n dU$-rN is used, an uracil DNA glycosylase and an apurinic endonuclease or working in an alkaline range will catalyse the cleavage of the $(rM)_n dU$ protecting group.

In the phosphorylation step the resulting polymer is phosphorylated or thiophosphorylated at the 5'-position using polynucleotide kinase, and the cycle may be started again.

The methods of preparation which have been schematically depicted in FIG. 2 should not be construed as limiting.

It will be recognized by the skilled artisan that also combinations of the methods shown are possible. Thus, primers of the general formula $p(dNp)_m$ may also be reacted with a carrier used according to the invention and having the general formula $(rM)_n dU$-rN and a primer of the general formula $p(rNp)_m$ may also be reacted with a carrier used according to the invention and having the general formula $(rM)_n dN$, respectively, to obtain polymers with a desired defined sequence. Further, a primer of the general formula $p(dNp)_m$ may also contain ribonucleotides and a primer of the general formula $p(rNp)_m$ may also contain deoxyribonucleotides, respectively.

RNA ligases have an extraordinary broad substrate specificity with respect to the donor. Thus, besides natural nucleotides, such as the mononucleoside 3',5'-bisphosphates (pNp), a number of modified nucleotides are active donors for RNA ligases. Modifications are possible at the base, such as lin-benzoadenosine, 5-fluorouridine, 5-iodouridine, 2-aminopurine, 2,6-diaminopurine, $N^6$-hexylaminoadenosine, at the sugar, for example 2'-O-methylguanosine, 2'-O-methyluridine, 2'-O-methylcytidine, and 2'-O-methoxyethylnucleosides, as well as at the phosphate groups, such as 5'-thiophosphoryl-pNp. Further modifications at the sugar besides 2'-O-methylribose analogues are also 2'-deoxyribose analogues or arabinose analogues. Modifications at the phosphate groups are phosphorothioates and phosphonates, while besides H-phosphonates also methyl phosphonates are substrates for RNA ligases.

It is known that β-substituted ADP derivatives [Ado-5'-PP-X] are also active substrates for RNA ligases in the ligation step. Nucleotide analogues having modifications at the base or at the sugar, nucleotides having an α-N glycosidic bond, phosphate esters of ribose, riboflavins, nicotinamide ribosides, pantetheines and cyanoethanol may be added as activated donors to the acceptor in the ligation step, such as adenylated nicotinamide riboside [Ado-5'PP5'-Nir], adenylated 8-bromo adenosine [Ado-5'PP5'-(8-BrAdo)], Ado-5'PP5'-riboflavin, adenylated 2'-fluoro adenosine [Ado-5'PP5'-(2'-FlAdo)], or Ado-5'PP6-cyanoethanol, where Ado represents the nucleoside adenosine.

As a result of the stereospecificity of RNA ligases the preparation of pure $R_p$ diastereoisomers or alternating $R_p/S_p$ isomers may be performed for the first time on an technical scale.

It has been surprisingly found that RNA ligases are also capable of forming a linkage between a 3'-phosphate donor and a 5'-hydroxyl acceptor. Activation of the donor at the 3'-position preferably takes place at high concentrations of ATP and an equimolar ratio of donor and acceptor. On the basis of these findings the two following methods for the preparation of polymers have been developed according to the present invention which are schematically illustrated in FIG. 3.

Figure 3:
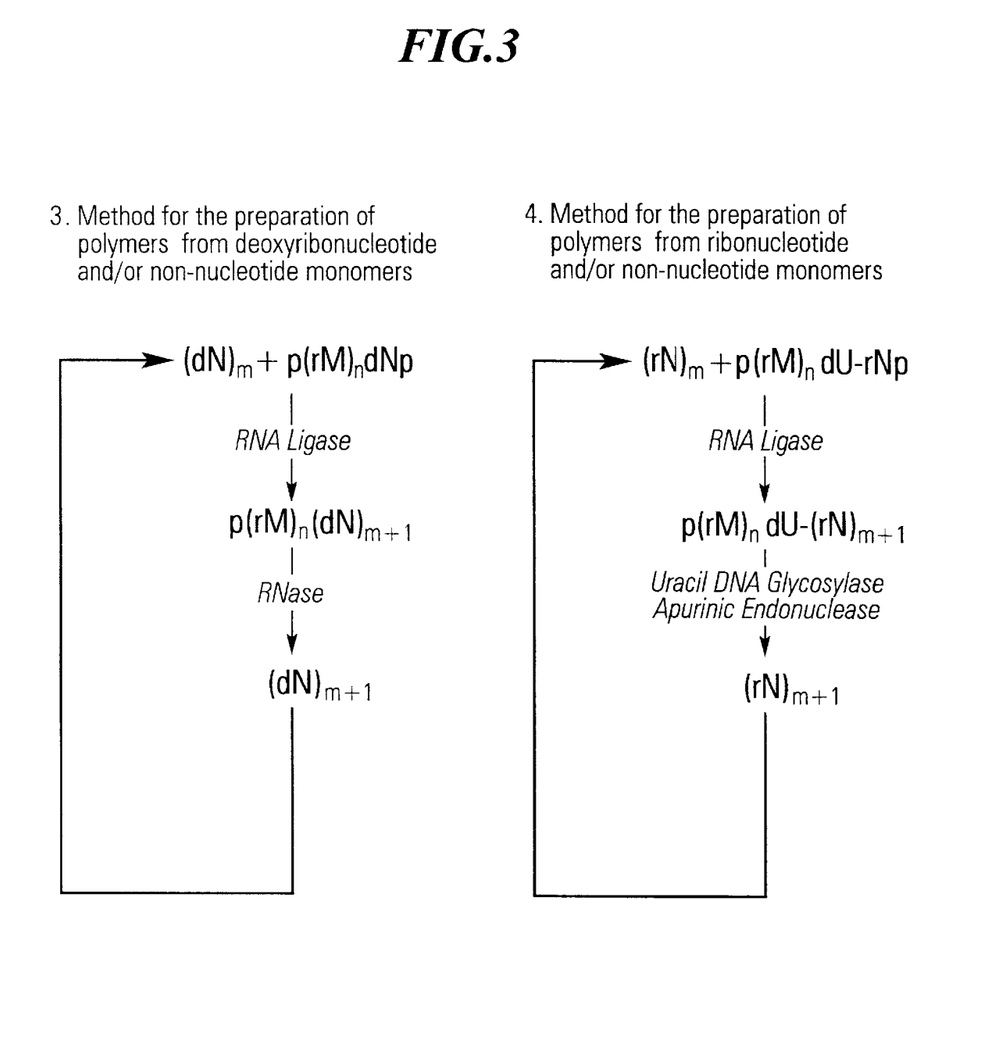
FIG. 3 is a pair of flow charts that illustrate third and fourth methods of the invention for preparing polymers from deoxyribonucleotide and/or non-nucleotide monomers and from ribonucleotide and/or non-nucleotide monomers.

The abbreviations used in FIG. 3 have the following meanings:

(dN)$_m$ primer (in this case the acceptor) in the method of preparation 3, (rN)$_m$ primer (in this case the acceptor) in the method of preparation 4, p(rM)$_n$dNp novel synthetic carrier: the donor in the method of preparation 3, p(rM)$_n$dU-rNp novel synthetic carrier: the donor in the method of preparation 4, rM a purine and/or pyrimidine ribonucleoside, dU a deoxyuridine, dN a natural and/or base- and/or sugar-modified deoxyribonucleoside and/or a non-nucleosidic ligation-competent group of compounds, rN a natural and/or base- and/or sugar-modified ribonucleoside and/or a non-nucleosidic ligation-competent group of compounds, p a phosphate and/or phosphorothioate and/or phosphonate, such as preferably methyl phosphonate and/or H-phosphonate, and/or phosphoramidate and/or formylacetal and/or phosphorodithioate and/or boranephosphate and/or phosphotriester group, m an integer of 1 or more, n is zero or an integer of 1 or more.

Starting with the carrier used according to the present invention (in this case the donor) of the general formula p(rM)$_n$dNp having the general structural formula IV p(rM)$_n$dNp and the novel carrier of the general formula p(rM)$_n$dU-rNp having the general structural formula V p(rM)$_n$dU-rNp and the primer (in this case the acceptor) of the general formula (dN)$_m$ or (rN)$_m$, respectively, having the general structural formula VI (dN)$_m$ and (rN)$_m$ wherein the abbreviations used in the formulas have the following meanings:

m an integer of 1 or more, n is zero or an integer of 1 or more

B a natural and/or modified purine and/or pyrimidine base,

U an uracil,

R$^1$ and R$^2$ H, OH, O-alkyl, F, J, Br, Cl, amino, aminoalkyl, O-alkoxyalkyl, alkyl X O, S, NH, —NR$^3$ (R$^3$=C$_{1\text{-}20}$-alkyl group)

p a phosphate and/or phosphorothioate and/or phosphonate, such as preferably methyl phosphonate and/or H-phosphonate, and/or phosphoramidate and/or formylacetal and/or phosphorodithioate and/or boranephosphate and/or phosphotriester group, wherein may be replaced by a non-nucleosidic ligation-competent group of compounds, the carrier used according to the present invention is first activated in the ligation step using RNA ligase, in an amount enabling ligation, and subsequently ligated to the primer.

Activation and ligation may occur together or separately.

The group p in the 3'-position of the carrier according to the invention of the general formula p(rM)$_n$dNp or p(rM)$_n$dU-rNp does not function as a protecting group. This group will not be removed in the deprotection step, but it will remain as a component of the finally defined sequence.

The carrier used according to the present invention having the general formula p(rM)$_n$dNp or p(rM)$_n$dU-rNp has p(rM)$_n$ or p(rM)$_n$dU as a protecting group in its 5'-position which will be removed in the deprotection step.

The primer and the carrier used according to the present invention may be present in the form of metal salts, preferably alkali metal salts.

In the deprotection step in the presence of an RNase digestion or alkaline cleavage of the p(rM)$_n$ protecting group occurs if the carrier having the general formula p(rM)$_n$dNp has been used. If the value of n is zero then it is not necessary to cleave off the p(rM)$_n$ protecting group since the resulting polymer already has the correct defined sequence. If the carrier having the general formula p(rM)$_n$dU-rNp is used, an uracil DNA glycosylase and an apurinic endonuclease or working in an alkaline range will catalyse cleavage of the p(rM)$_n$dU protecting group.

The cycle may be started again.

The methods of preparation according to the present invention which have been schematically depicted in FIG. 3 should not be construed as limiting.

It will be recognized by the skilled artisan that also combinations of the methods shown are possible. Thus, primers of the general formula $(dN)_m$ may be reacted with a carrier used according to the invention having the general formula $p(rM)_n dU-rNp$ and an primer of the general formula $(rN)_m$ may also be reacted with a carrier used according to the invention having the general formula $p(rM)_n dNp$, respectively, to obtain polymers with a desired defined sequence. Further, a primer of the general formula $(dN)_m$ may also contain ribonucleotides and a primer of the general formula $(rN)_m$ may also contain deoxyribonucleotides, respectively.

EXAMPLES FOR THE SYNTHESIS OF POLYMERS

Figure 4:
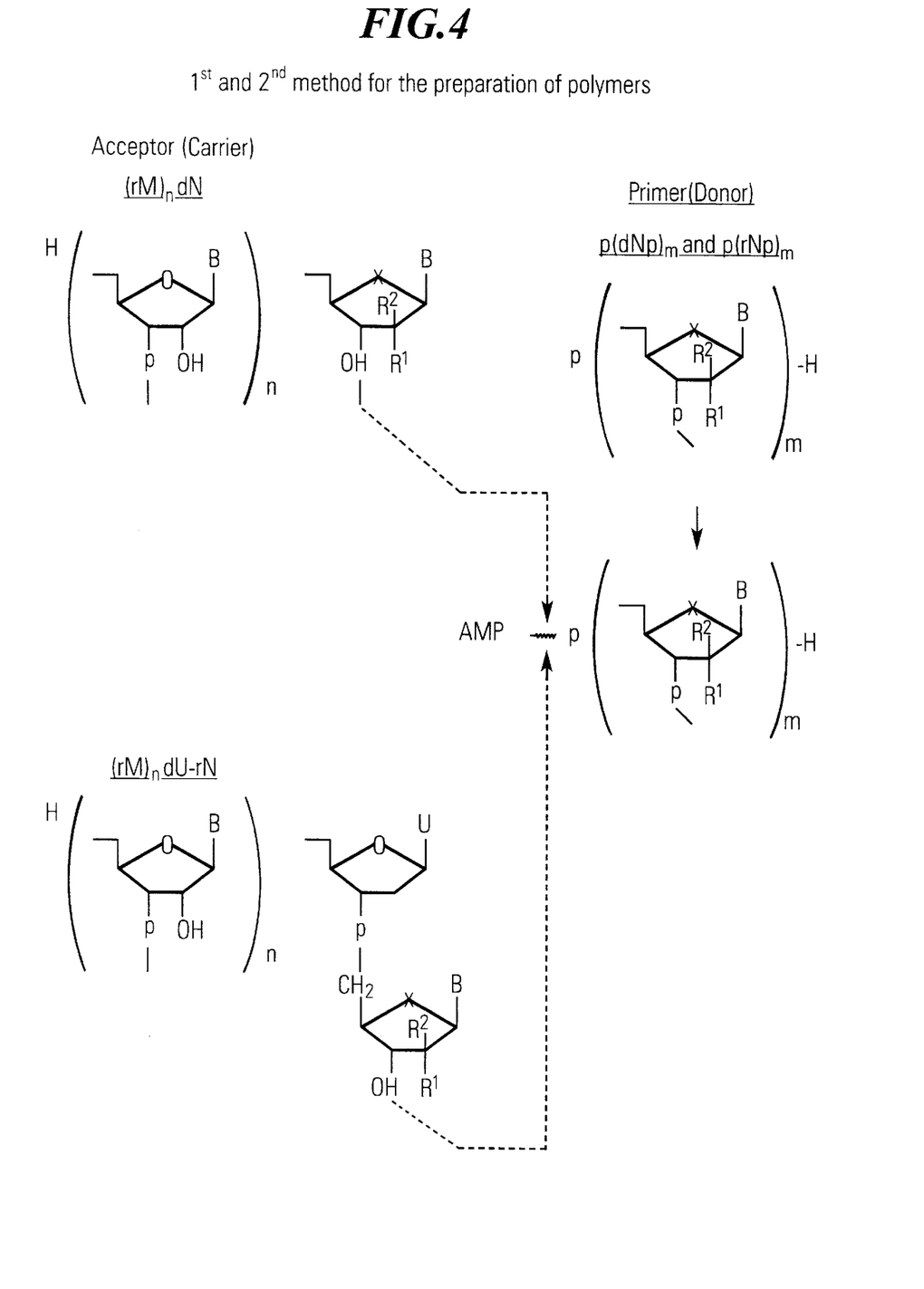
FIG. 4 is a flow chart that further illustrates the first and second methods for preparing polymers according to the invention.
Figure 5:
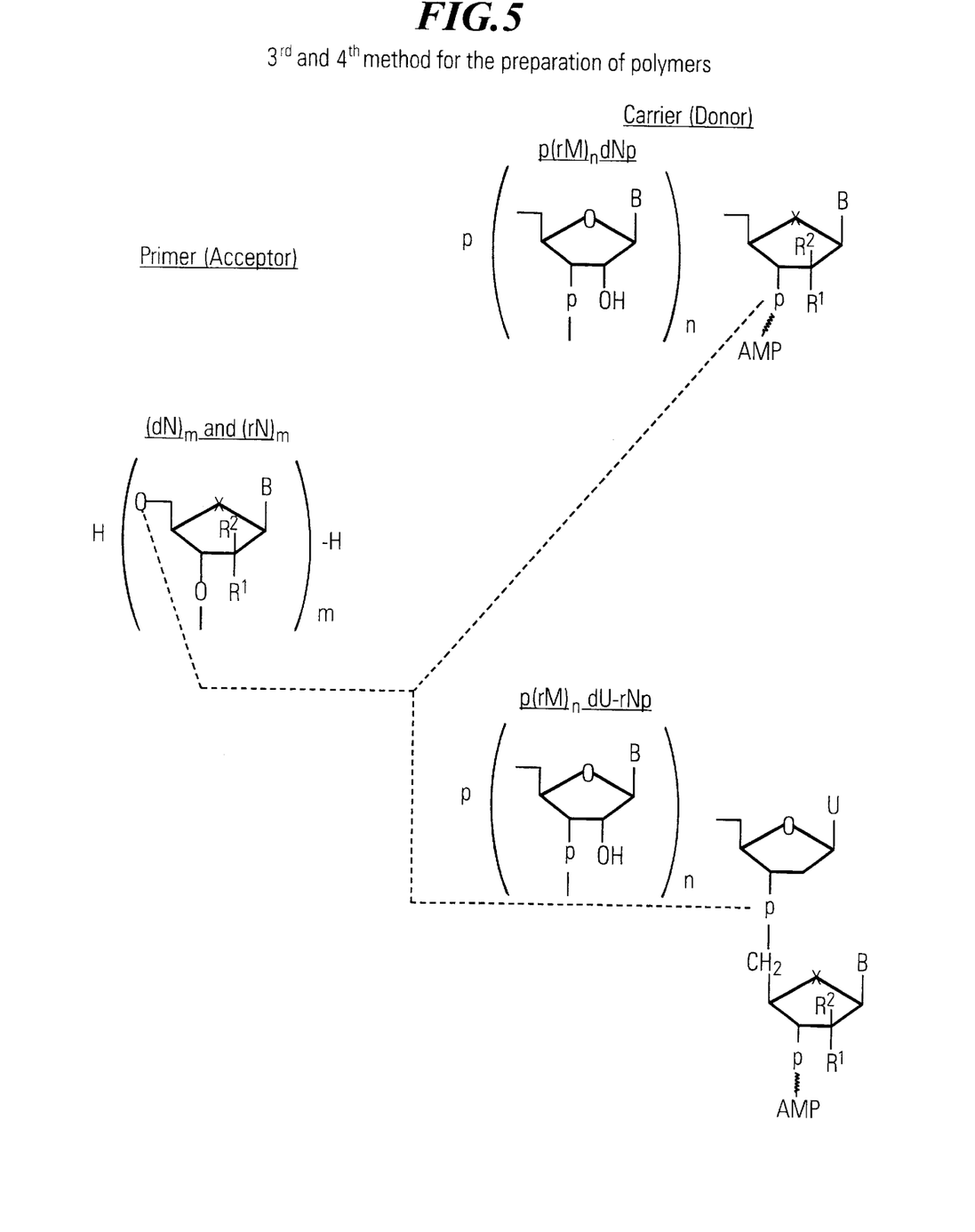
FIG. 5 is a flow chart that further illustrates the third and fourth methods for preparing polymers according to the invention.

The examples illustrate the methods according to the present invention. They are schematically depicted in FIGS. 4 and 5. The examples should not be construed as limiting.

Example 1: Method of Preparation 1

In the ligation step comprising activation and ligation, the primer of the general formula $p(dNp)_m$ was first activated in the presence of a RNA ligase with ATP, 50 mM HEPPS-NaOH as the buffer at a pH of approx. 8.3, 10 mM $MnCl_2$, 20 mM DTT, 10 µg/ml bovine serum albumine (BSA) at a temperature of 30 to 35° C. Within the first 3 hours the activation step achieved a yield of 96.8% of activated primer. During the subsequent ligation step the remaining 3.2% were completely reacted. In this step, the activated primer was ligated with the carrier used according to the invention having the general formula $(rM)_n dN$ under the same conditions as mentioned above, but without ATP. The ligation reaction proceeded with 100% conversion of the activated primer within about 4.5 hours. Additional information about the identity of the ligation product was provided by alkaline phosphatase treatment as well as mass spectrometric measurement.

Activation and ligation may take place together or separately under reaction conditions as mentioned for the ligation step.

By achieving 100% of conversion in a short time the most difficult technological problems: activation and ligation, which play a key role in the practice of a technical method of preparation of polymers have been solved.

In the deprotection step, cleavage of the $(rM)_n$ protecting group wherein $n \geq 1$ was carried out, if the carrier according to the invention of the general formula $(rM)_n dN$ was used, in the presence of an RNase under the conditions mentioned in the ligation step at a temperature of about 37° C., or alkaline cleavage of the $(rM)_n$ protecting group was carried out by raising the pH to about 10.0 to 11.5. Cleavage of the protecting group of the general formula $(rM)_n$ was achieved within a few minutes.

In the phosphorylation step the polymer was phosphorylated or thiophosphorylated using a polynucleotide kinase at a temperature of about 37° C. and otherwise using the same conditions as those in the ligation step. In this step, a polynucleotide kinase catalyzed the transfer of the terminal phosphate group of ATP or ATP-γ-S, where ATP-γ-S is adenosine 5'-O-(3-thiotriphosphate), to the 5'-hydroxyl group of the product. The reaction proceeded in 2–3 minutes with a yield of 100%.

The cycle could be started again until a polymer of desired length and defined monomer sequence was formed. The next coupling was performed under the conditions mentioned in the ligation step in 3.5 hours also achieving a yield of about 100%. Shorter reaction times could be used if higher enzyme concentrations were employed. Preferably, the reaction conditions were identical for all reaction steps and are described for the ligation step. The courses of all reactions were analyzed by means of HPLC.

As the primer of general formula $p(dNp)_m$ there may be for example used $p(dAp)_m$, $p(dCp)_m$, $p(dGp)_m$, $p(dTp)_m$, or combinations of the bases A, C, G, and T as well as p(lin-benzodeoxyadenosine 3'-phosphate)$_m$, p(2-aminodeoxyadenosine 3'-phosphate)$_m$, p(2-aminoalkyldeoxyadenosine 3'-phosphate)$_m$, p(2-heterocycloalkyldeoxyadenosine 3'-phosphate)$_m$, p(5-methyldeoxycytidine 3'-phosphate)$_m$, p(5-propinyldeoxycytidine 3'-phosphate)$_m$, p(5-iododeoxyuridine 3'-phospbate)$_m$, p(iso-deoxycytidine 3'-phosphate)$_m$, p(7-propinyl-deaza deoxyguanosine 3'-phosphate)$_m$, p(7-propinyl deaza deoxyadenosine 3'-phosphate)$_m$, p(2'-O-methylcytidine 3'-phosphate)$_m$, p(2'-O-methoxyethylguanosine 3'-phosphate)$_m$, p(ara-G 3'-phosphate)$_m$, p(2-nitrophenylmethanol)$_m$, p(nitrophenol)$_m$, p(methoxyphenol)$_m$, p(2,6-diaminopurine 3'-pbosphate)$_m$, (2'-deoxyguanosine 3'-phosphate 5'-thiophosphate)$_m$, p(dC 3'-thiophosphate)$_m$ and others may be used.

As the carrier according to the present invention of the general formula $(rM)_n dN$ there may be for example used $(rG)_n dC$, $(rA)_n 2'$-O-methylcytidine, $(rA)_n dG$, $(rG)_n 2$-amninodeoxyadenosine, $(rC)_n 2$-aminoalkyldeoxyadenosine, $(rU)_n 2$-heterocycloalkyldeoxyadenosine, $(rA)_n 5$-methyldeoxycytidine, $(rG)_n 5$-propinyldeoxycytidine, $(rC)_n 2'$-O-methoxyethylguanosine, $(rG)_n N^6$-hexylaminodeoxyadenosine, $(rU)_n araG$, $(rC)_n 2'$-O-methyladenosine, $(rC)_n 7$-propinyldeazadeoxyguanosine, $(rG)_n 7$-propinyldeazadeoxyadenosine, $(rG)_n 6$-cyanoethanol, $(rG)_n 5$-methyldeoxycytidine, $(rA)_n 2,6$-diaminopurine and others.

Example 2: Method of Preparation 2

In the ligation step comprising activation and ligation, the primer of the general formula $p(rNp)_m$ was first activated in the presence of a RNA ligase with ATP, 50 mM HEPPS-NaOH as the buffer at a pH of approx. 8.3, 10 mM $MnCl_2$, 20 mM DTT, 10 µg/ml bovine serum albumine (BSA) at a temperature of 30 to 35° C. Within the first 3 hours the activation step achieved a yield of 96.8% of activated primer. During the subsequent ligation step the remaining 3.2% were completely reacted. In this step, the activated primer was ligated with the carrier used according to the invention having the general formula $(rM)_n dU-rN$ under the same conditions as mentioned above, but without ATP. The ligation reaction proceeded with 100% conversion of the activated primer within about 4.5 hours. Additional information about the identity of the ligation product was provided by alkaline phosphatase treatment as well as mass spectrometric measurement.

Activation and ligation may take place together or separately under reaction conditions as mentioned above for the ligation step.

By achieving 100% of reaction in a short time the most difficult technological problems: activation and ligation, which play a key role in the practice of a technical method of preparation of polymers have been solved.

In the deprotection step, cleavage of the $(rM)_n dU$ protecting group, if the carrier of the invention having the general formula $(rM)_n dU-rN$ was used, was carried out in the presence of a uracil DNA glycosylase and an apurinic endonuclease under the conditions mentioned in the ligation step at a temperature of about 37° C., or alkaline cleavage of the $(rM)_n dU$ protecting group was carried out by raising the pH to about 10.0 to 11.5. Cleavage of the protecting group of the general formula $(rM)_n dU$ was achieved within a few minutes.

In the phosphorylation step the polymer was phosphorylated or thiophosphorylated using a polynucleotide kinase at a temperature of about 37° C. and otherwise using the same conditions as those in the ligation step. In this step, a polynucleotide kinase catalyzed the transfer of the terminal phosphate group of ATP or ATP-γ-S, where ATP-γ-S is adenosine 5'-O-(3-thiotriphosphate), to the 5'-hydroxyl group of the product. The reaction proceeded in 2–3 minutes with a yield of 100%.

The cycle could be started again until a polymer of desired length and defined monomer sequence was formed. The next coupling was performed under the conditions mentioned for the ligation step in 3.5 hours also achieving a yield of about 100%. Shorter reaction times could be used if higher enzyme concentrations were employed. Preferably, the reaction conditions were identical for all reaction steps and are described for the ligation step. The courses of all reactions were analysed by means of HPLC.

As the primer of the general formula $p(rNp)_m$ there may be for example used $p(rAp)_m$, $p(rCp)_m$, $p(rGp)_m$, $p(rTp)_m$, or combinations of the bases A, C, G, and T as well as p(lin-benzoadenosine 3'-phosphate)$_m$, p(2-aminoadenosine 3'-phosphate)$_m$, p(2-aminoalkyladenosine 3'-phosphate)$_m$, p(2-heterocycloalkyladenosine 3'-phosphate)$_m$, p(5-methylcytidine 3'-phosphate)$_m$, p(5-propinylcytidine 3'-phosphate)$_m$, p(5-iodouridine 3'-phosphate)$_m$, p(iso-cytidine 3'-phosphate)$_m$, p(7-propinyl-deaza guanosine 3'-phosphate)$_m$, p(7-propinyl-deaza adenosine 3'-phosphate)$_m$, p(2'-O-methylcytidine 3'-phosphate)$_m$, p(2'-O-methoxyethylguanosine 3'-phosphate)$_m$, p(ara-G 3'-phosphate)$_m$, p(2-nitrophenylmethanol)$_m$, p(nitrophenol)$_m$, p(methoxyphenol)$_m$, p(2,6-diaminopurine 3'-phosphate)$_m$, (guanosine 3'-phosphate 5'-thiophosphate)$_m$, (cytidine 3'-thiophosphate 5'-phosphate)$_m$ and others may be used.

As the carrier according to the present invention of the general formula $(rM)_n dU$-rN there may be for example used $(rG)_n dU$-rC, $(rA)_n dU$-2'-O-methylcytidine, $(rA)_n dU$-rG, $(rG)_n dU$-2-aminoadenosine, $(rC)_n dU$-2-aminoalkyladenosine, $(rU)_n dU$-2-heterocycloalkyladenosine, $(rA)_n dU$-5-methylcytidine, $(rG)_n dU$-5-propinylcytidine, $(rC)_n$-dU-2'-O-methoxyethylguanosine, $(rG)_n dU$-N$^6$-hexylaminoadenosine, $(rU)_n dU$-araG, $(rC)_n dU$-2'-O-methyladenosine, $(rC)_n dU$-7-propinyldeazaguanosine, $(rG)_n dU$-7-propinyldeaza-adenosine, $(rG)_n dU$-6-cyanoethanol, $(rA)_n dU$-2,6-diaminopurine and others.

Example 3: Method of Preparation 3

In the ligation step comprising activation and ligation, the carrier used according to the invention of the general formula $p(rM)_n dNp$ was first activated in the presence of a RNA ligase with ATP, 50 mM HEPPS-NaOH as the buffer at a pH of approx. 8.3, 10 mM MnCl$_2$, 20 mM DTT, 10 μg/ml bovine serum albumine (BSA) at a temperature of 30 to 35° C. Within the first 3 hours the activation step achieved a yield of 96.8% of activated carrier. During the subsequent ligation step the remaining 3.2% were completely reacted. In this step, the activated carrier was ligated with the primer having the general formula $(dN)_m$ under the same conditions as mentioned above, but without ATP. The ligation reaction proceeded with 100% conversion of the activated primer within about 4.5 hours. Additional information about the identity of the ligation product was provided by alkaline phosphatase treatment as well as mass spectrometric measurement.

Activation and ligation may take place together or separately under reaction conditions as mentioned for the ligation step.

By achieving 100% of reaction in a short time the most difficult technological problems: activation and ligation, which play a key role in the practice of a technical method of preparation of polymers have been solved.

In the deprotection step, cleavage of the $p(rM)_n$ protecting group wherein $n \geq 1$ was carried out, if the carrier according to the invention of the general formula $p(rM)_n dNp$ was used, in the presence of an RNase under the conditions mentioned in the ligation step at a temperature of about 37° C., or alkaline cleavage of the $p(rM)_n$ protecting group was carried out by raising the pH to about 10.0 to 11.5. Cleavage of the protecting group of the general formula $p(rM)_n$ was achieved within a few minutes.

The cycle could be started again until a polymer of desired length and defined monomer sequence was formed. The next coupling was performed under the conditions mentioned for the ligation step in 3.5 hours also achieving a yield of about 100%. Shorter reaction times could be used if higher enzyme concentrations were employed. Preferably, the reaction conditions were identical for all reaction steps and are described for the ligation step. The courses of all reactions were analysed by means of HPLC.

As the primer of general formula $(dN)_m$ there may be for example used $(dA)_m$, $(dC)_m$, $(dG)_m$, $(dT)_m$, or combinations of the bases A, C, G, and T as well as (lin-benzodeoxyadenosine)$_m$, (2-aminodeoxyadenosine)$_m$, (2-aminoalkyldeoxyadenosine)$_m$, (2-heterocycloalkyldeoxyadenosine)$_m$, (5-methyldeoxycytidine)$_m$, (5-propinyldeoxycytidine)$_m$, (5-iododeoxyuridine)$_m$, (iso-deoxycytidine)$_m$, (7-propinyl-deaza deoxyguanosine)$_m$, (7-propinyl-deaza deoxyadenosine)$_m$, (2'-O-methylcytidine)$_m$, (2'-O-methoxyethylguanosine)$_m$, (ara-guanosine)$_m$, (2-nitrophenylmethanol)$_m$, (nitrophenol)$_m$, (methoxyphenol)$_m$, (2,6-diaminopurine)$_m$, and others may be used.

As the carrier according to the present invention of the general formula $p(rM)_n dNp$ there may be for example used $p(rG)_n dC$ 3'-phosphate, $p(rA)_n dG$ 3'-phosphate, $p(rA)_n 2$'-O-methylcytidine 3'-phosphate, $p(rG)_n 2$-aminodeoxyadenosine 3'-phosphate, $p(rC)_n 2$-aminoalkyldeoxyadenosine 3'-phosphate, $p(rU)_n 2$-heterocycloalkyldeoxyadenosine 3'-phosphate, $p(rA)_n 5$-methyldeoxycytidine 3'-phosphate, $p(rG)_n 5$-propinyldeoxycytidine 3'-phosphate, p(rC)-2'-O-methoxyethylguanosine 3'-phosphate, $p(rG)_n N^6$-hexylaminodeoxyadenosine 3'-phosphate, $p(rU)_n$araG 3'-phosphate, $p(rC)_n 2$'-O-methyladenosine 3'-phosphate, $p(rC)_n 7$-propinyldeazadeoxyguanosine 3'-phosphate, $p(rG)_n 7$-propinyldeazadeoxyadenosine 3'-phosphate, $p(rG)_n 6$-cyanoethanol, $p(rG)_n 5$-methyldeoxycytidine 3'-phosphate, $p(rA)_n 2,6$-diaminopurine 3'-phosphate, $p(rA)_n dC$ 3'-thiophosphate, $p(rA)_n dC$ 3'-methylphosphonate, $p(rG)_n dC$ 3'-H-phosphonate, $p(rG)_n dA$ 3'-phosphoramidate, $p(rU)_n dG$ 3'-formylacetal, $p(C)_n dG$ 3'-phosphorodithioate, $p(rA)_n dC$ 3'-boranephosphonate, $p(rG)_n dG$ 3'-phosphotriester and others.

Example 4: Method of Preparation 4

In the ligation step comprising activation and ligation, the carrier used according to the invention of the general formula $p(rM)_n dU\text{-}rNp$ was first activated in the presence of a RNA ligase with ATP, 50 mM HEPPS-NaOH as the buffer at a pH of approx. 8.3, 10 mM $MnCl_2$, 20 mM DTT, 10 µg/ml bovine serum albumine (BSA) at a temperature of 30 to 35° C. Within the first 3 hours the activation step achieved a yield of 96.8% of activated carrier. During the subsequent ligation step the remaining 3.2% were completely reacted. In this step, the activated carrier was ligated with the primer having the general formula $(rN)_m$ under the same conditions as mentioned above, but without ATP. The ligation reaction proceeded with 100% conversion of the activated primer within about 4.5 hours. Additional information about the identity of the ligation product was provided by alkaline phosphatase treatment as well as mass spectrometric measurement.

Activation and ligation may take place together or separately under reaction conditions as mentioned above for the ligation step.

By achieving 100% reaction in a short time the most difficult technological problems: activation and ligation, which play a key role in the practice of a technical method of preparation of polymers have been solved.

In the deprotection step, cleavage of the $p(rM)_n dU$ protecting group was carried out if a carrier according to the invention of the general formula $p(rM)_n dU\text{-}rNp$ was used in the presence of an uracil DNA glycosylase and an apurinic endonucleoase under the conditions mentioned in the ligation step at a temperature of about 37° C., or alkaline cleavage of the $p(rM)_n dU$ protecting group was carried out by raising the pH to about 10.0 to 11.5. Cleavage of the protecting group of the general formula $p(rM)_n dU$ was achieved within a few minutes.

The cycle could be started again until a polymer of desired length and defined monomer sequence was formed. The next coupling was performed under the conditions mentioned for the ligation step in 3.5 hours also achieving a yield of about 100%. Shorter reaction times could be used if higher enzyme concentrations were employed. Preferably, the reaction conditions were identical for all reaction steps and are described for the ligation step. The courses of all reactions were analysed by means of HPLC.

As the primer of general formula $(rN)_m$ there may be for example used $(rA)_m$, $(rC)_m$, $(rG)_m$, $(rT)_m$, or combinations of the bases A, C, G, and T as well as $(lin\text{-}benzoadenosine)_m$, $(2\text{-}aminoadenosine)_m$, $(2\text{-}aminoalkyladenosine)_m$, $(2\text{-}heterocycloalkyladenosine)_m$, $(5\text{-}methylcytidine)_m$, $(5\text{-}propinylcytidine)_m$, $(5\text{-}iodouridine)_m$, $(iso\text{-}cytidine)_m$, $(7\text{-}propinyl\text{-}deaza\ guanosine)_m$, $(7\text{-}propinyl\text{-}deaza\ adenosine)_m$, $(2'\text{-}O\text{-}methylcytidine)_m$, $(2'\text{-}O\text{-}methoxyethylguanosine)_m$, $(ara\text{-}guanosine)_m$, $(2\text{-}nitrophenylmethanol)_m$, $(nitrophenol)_m$, $(methoxyphenol)_m$, $(2,6\text{-}diaminopurine)_m$, and others may be used.

As the carrier according to the present invention of the general formula $p(rM)_n dU\text{-}rNp$ there may be for example used $p(rG)_n dU\text{-}rC$ 3'-phosphate, $p(rA)_n dU\text{-}rG$ 3'-phosphate, $p(rA)_n dU\text{-}2'\text{-}O\text{-}methylcytidine$ 3'-phosphate, $p(rG)_n dU\text{-}2\text{-}aminoadenosine$ 3'-phosphate, $p(rC)_n dU\text{-}2\text{-}aminoalkyladenosine$ 3'-phosphate, $p(rU)_n dU\text{-}2\text{-}heterocycloalkyladenosine$ 3'-phosphate, $p(rA)_n dU\text{-}5\text{-}methylcytidine$ 3'-phosphate, $p(rG)_n dU\text{-}5\text{-}propinylcytidine$ 3'-phosphate, $p(rC)_n\text{-}dU\text{-}2'\text{-}O\text{-}methoxyethylguanosine$ 3'-phosphate, $p(rG)_n dU\text{-}N^6\text{-}hexylaminoadenosine$ 3'-phosphate, $p(rU)_n dU\text{-}araG$ 3'-phosphate, $p(rC)_n dU\text{-}2'\text{-}O\text{-}methyladenosine$ 3'-phosphate, $p(rC)_n dU\text{-}7\text{-}propinyldeazaguanosine$ 3'-phosphate, $p(rG)_n dU\text{-}7\text{-}propinyldeaza\ adenosine$ 3'-phosphate, $p(rG)_n dU\text{-}6\text{-}cyanoethanol$, $p(rA)_n dU\text{-}2,6\text{-}diaminopurine$ 3'-phosphate, $p(rA)_n dU\text{-}rC$ 3'-thiophosphate, $p(rG)_n dU\text{-}rC$ 3'-methylphosphonate, $p(rG)_n dC$ 3'-H-phosphonate, $p(rG)_n dA$ 3'-phosphoramidate, $p(rU)_n dG$ 3'-formylacetal, $p(C)_n dU\text{-}rG$ 3'-phosphorodithioate, $p(rA)_n dU\text{-}rC$ 3'-boranephosphonate, $p(rG)_n dU\text{-}rG$ 3'-phosphotriester and others.

ISOLATION AND PURIFICATION OF POLYMERS

To isolate and purify polymer mixtures several chromatographic methods may be used. Preferably, these include high pressure liquid chromatography (HPLC) on an analytical scale, and anion exchange chromatography on a technical scale.

Example 5: Isolation and Purification of Polymers on an Analytical Scale

Preferably, RP-HPLC chromatography is used to analytically separate polymer mixtures. The column materials employed in RP-HPLC have a narrow diameter of 5–7 µm and, thus, enable a high packing density of the column. RP-HPLC provides a higher resolution, and the time required for elution of the compounds to be separated is highly reduced. To decrease the retention time and the elution sharpness of the polymers, the polarity of the solvent employed, such as methanol or acetonitrile, is continuously decreased (gradient elution). As the reversed phase matrix there is used chemically modified silica (Eurospher 100 C18, Knauer GmbH company, Germany) and as the eluent there is used $KH_2PO_4$ 50 mM in water and methanol. Depending on the hydrophobicity of the polymer, the methanol concentration varies between 2.5% and 25%.

Example 6: Purification and Isolation of Polymers on a Technical Scale

For the separation of polymer mixtures on a technical scale, column chromatography on anion exchangers, such as Dowex-AG 1-X2, DEAE cellulose, DEAE sephadex, source 15Q or source 30Q, may be suitably used. Generally, the elution is performed by a linear salt gradient with increasing salt concentration. Preferably, since for further reactions the recovered polymers are mostly required to be salt-free, an ammonium bicarbonate buffer, an ammonium acetate buffer, or a triethyl ammonium bicarbonate buffer (TEAB) is used which by lyophilization or distillation under reduced pressure in a rotary evaporator at low temperature may be removed without any residue.

AUTOMATIZATION

Thus, the methods of the invention may be used:

for automatization on a small scale for the preparation of a variety of polymers as well as on a technical scale for the preparation of active agents for therapeutics.

For enzymatic preparation of polymers from nucleotide and/or non-nucleotide monomers there are several possibilities according to the present invention.

Example 7: Method for the Preparation of Polymers in a Batch Method

The method according to the invention for the preparation of polymers may be performed in a batch method. All enzymes, such as RNA ligases, RNases, uracil DNA glycosylases, apurinic endonucleases and the polynucleotide kinases, are inactivated after each reaction step. The main problem is the inactivation of a RNase. However, inactivation is indispensable, since an active RNase in a new coupling step would attack and degrade the carrier molecules of the invention of the methods of preparation 1 and 3 so that a ligation reaction would no longer be possible. It is known that most RNases are very thermostable enzymes which may not be inactivated by heat (temperatures of 95° C.). From the literature a number of different RNase inhibitors are known, such as heat labile RNase inhibitor proteins, vanadyl ribonucleoside complex, and also bentonite. All RNases may be hydrolysed using proteases such as proteinase K. Incubation with a proteinase K at about 37° C. and subsequent heat inactivation is an effective means to inactivate a RNase. The RNA ligases, uracil DNA glycosylases, apurinic endonucleases and the polynucleotide kinases are also inactivated by heat.

Example 8: Method of Preparation of Polymers with Immobilized Enzymes

The method according to the present invention for the preparation of polymers on a technical scale may also be carried out using immobilized enzymes in reactors in a continuous method. The enzymes are not inactivated but by immobilization on a carrier material remain in the reactor for further coupling steps. The use of enzyme-membrane reactors with membranes of 10 kDA also enables the use of the enzymes for a number of coupling steps in a continuous method.

Because of the high substrate specificity of RNA ligases it is possible to enzymatically prepare all generations of nucleotidic and non-nucleotidic polymers having a defined sequence and length in 3'→5' direction.

REFERENCES

/1/ Hyman, E.D., U.S. Pat. No. 5,436,143 (1995)

/2/ Hyman, E.D., U.S. Pat. No. 5,516,664 (1996)

/3/ ISIS PHARMACEUTICALS, Inc., U.S. Pat. No. 5,576,302 (1996)

/4/ Gen-Probe, Inc., U.S. Pat. No. 5,739,311 (1998)

/5/ Moseman et al., Biochemistry, 19, 635–642 (1980)

/6/ Petric et al., Nucleic Acids Res., 19, 585 (1990)

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspect, advantages, and modifications are within the scope of the following claims.

What is claimed is:

1. A method for preparing nucleotide polymers having a defined monomer sequence by polymerization in the 3' to 5' direction, the method comprising
   a) providing a primer of the general formula $p(dNp)_m$ or $p(rNp)_m$ and a carrier molecule of the general formula $(rM)_n dN$ or $(rM)_n dU$-rN where
      p is a phosphate group, a phosphorothioate group, a phosphonate group, a methyl-phosphonate group, a phosphoramidate group, a formylacetyl group, a phosphorodithioate group, a boranephosphate group, or a phosphotriester group;
      dN is a natural or modified deoxyribonucleoside;
      rN is a natural or modified ribonucleoside;
      m is an integer of 1 or more;
      rM is a purine or pyrimidine ribonucleoside;
      n is an integer of 1 or more; and
      dU is a deoxyuridine;
   b) ligating the 3' end of the carrier molecule to the 5' position of the primer with RNA ligase; thereby obtaining a ligation product;
   c) deprotecting the ligation product by removing $(rM)_n$ when using a carrier molecule of the general formula $(rM)_n dN$ or removing $(rM)_n dU$ when using a carrier molecule of the general formula $(rM)_n dU$-rN;
   d) transferring a natural or modified phosphate group to the 5' position of the ligation product;
   e) optionally repeating steps (a) to (d); and
   f) optionally purifying the ligation product.

2. A method for preparing nucleotide polymers having a defined monomer sequence by polymerization in the 3' direction, the method comprising
   a) providing a primer of the general formula $(dN)_m$ or $(rN)_m$ and a carrier molecule of the general formula $p(rM)_n dNp$ or $p(rM)_n dU$-rNp where
      p is a phosphate group, a phosphorothioate group, a phosphonate group, a methyl-phosphonate group, a phosphoramidate group, a formylacetyl group, a phosphorodithioate group, a boranephosphate group, or a phosphotriester group;
      dN is a natural or modified deoxyribonucleoside;
      rN is a natural or modified ribonucleoside;
      m is an integer of 1 or more;
      rM is a purine or pyrimidine ribonucleoside;
      n is an integer of 1 or more; and
      dU is a deoxyuridine;
   b) ligating the 3' end of the carrier molecule to the 5' position of the primer with RNA ligase; thereby obtaining a ligation product;
   c) deprotecting the ligation product by removing $p(rM)_n$ when using a carrier molecule of the general formula $p(rM)_n dNp$ or removing $p(rM)_n dU$ when using a carrier molecule of the general formula $p(rM)_n dU$-rNp;
   d) optionally repeating steps (a) to (c); and
   e) optionally purifying the ligation product.

3. The method of claim 1, wherein if the carrier molecule is $(rM)_n dN$, the ligation product is deprotected with RNase.

4. The method of claim 1, wherein if the carrier molecule is $(rM)_n dU$-rN, the ligation product is deprotected with uracil DNA glycosylase and an apurinic endonuclease or with alkaline treatment.

5. The method of claim 2, wherein if the carrier molecule is $p(rM)_n dNp$, the ligation product is deprotected with RNase.

6. The method of claim 2, wherein if the carrier molecule is of the general formula $p(rM)_n dU$-rNp, the ligation product is deprotected with uracil DNA glycosylase and an apurinic endonuclease or with alkaline treatment.

7. The method of claim 1, wherein the phosphate group is modified.

8. The method of claim 2, wherein the phosphate group is modified.

9. The method of claim 1, wherein the method is carried out in a batch process and the enzymes employed in each step are deactivated after each step.

10. The method of claim 2, wherein the method is carried out in a batch process and the enzymes employed in each step are deactivated after each step.

11. The method of claim 1, wherein the method is carried out with immobilized enzymes or in enzyme membrane reactors, and the enzymes are not deactivated.

12. The method of claim 2, wherein the method is carried out with immobilized enzymes or in enzyme membrane reactors, and the enzymes are not deactivated.

13. The method of claim 1, wherein steps (b), (c), and (d) are carried out in a temperature range between 4° and 40° C. and in a pH range between 7.0 and 10.0.

14. The method of claim 2, wherein steps (b) and (c) are carried out in a temperature range between 4° and 40° C. and in a pH range between 7.0 and 10.0.

15. The method of claim 1, wherein step (b) is carried out in a reaction medium buffered with 4-(2-Hydroxyethyl) piperazine-1-propanesulfonic acid-NaOH (HEPPS-NaOH).

16. The method of claim 2, wherein step (b) is carried out in a reaction medium buffered with 4-(2-Hydroxyethyl) piperazine-1-propanesulfonic acid-NaOH (HEPPS-NaOH).

17. The method of claim 1, wherein stop (b) is carried out in a reaction medium containing DMSO.

18. The method of claim 2, wherein step (b) is carried out in a reaction medium containing DMSO.

19. The method of claim 1, wherein the primer of the general formula $p(dNp)_m$ or $p(rNp)_m$ comprises mixed residues dN and rN.

20. The method of claim 2, wherein the primer of the general formula $(dN)_m$ or $(rN)_m$ comprises mixed residues dN and rN.

21. A method for preparing polymers having a defined sequence from nucleotide or non-nucleotide monomers by polymerization in the 3' to 5' direction, the method comprising ligating a primer comprising one or more natural or modified ribonucleosides or deoxyribonucleosides to a carrier molecule with RNA ligase, the carrier molecule comprising a protecting group at a 5' position of a natural or modified nucleoside monomer or lacking a protecting group at a 3' position.

22. A method for preparing natural or modified polymers of nucleotide or non-nucleotide monomers, having a defined monomer sequence, by polymerization in the 3' to 5' direction, the method comprising a) providing a synthetic carrier molecule comprising the general formula $(rM)_n dN$ or $p(rM)_n dNp$ or $(rM)_n dU\text{-}rN$ or $p(rM)_n dU\text{-}rNp$ where
   rM is a purine or pyrimidine ribonucleoside and where each rM in a series can be the same or different;
   n is an integer of 1 or more;
   dN is a natural or modified deoxyribonucleoside;
   dN is a natural or modified deoxyribonucleoside;
   p is a phosphate group, a phosphorothioate group, a phosphonate group, a methyl-phosphonate group, a phosphoramidate group, a formylacetyl group, a phosphorodithioate group, a boranephosphate group, or a phosphotriester group;
   rN is a natural or modified ribonucleoside; and
   dU is a deoxyuridine;

b) providing a natural or modified nucleotide primer comprising one or more natural or modified ribonucleosides or deoxyribonucleosides; and c) ligating the primer to the carrier molecule with RNA ligase.

* * * * *